United States Patent [19]

Ruffa

[11] 4,415,089

[45] Nov. 15, 1983

[54] SUTURE AND SURGICAL ACCESSORY RACK

[76] Inventor: Rose Ruffa, R.D. 2 Farberhill Rd., Boonton Township, Morris County, N.J. 07005

[21] Appl. No.: 317,588

[22] Filed: Nov. 3, 1981

[51] Int. Cl.³ .............................................. A47F 7/00
[52] U.S. Cl. ..................................... 211/13; 206/63.3; 206/363; 206/370
[58] Field of Search ............. 211/13; 128/303 R, 1 R; 297/191; 206/63.3, 363, 370; 248/507

[56] References Cited

U.S. PATENT DOCUMENTS

| | | | |
|---|---|---|---|
| 921,796 | 5/1909 | Chambers, Jr. | 248/507 X |
| 2,588,529 | 3/1952 | Hume | 211/13 X |
| 2,733,113 | 1/1956 | Humbargar | 211/13 X |
| 3,479,085 | 11/1969 | Weinstein | 297/191 X |
| 3,819,039 | 6/1974 | Erickson | 206/63.3 X |
| 3,861,521 | 1/1975 | Burtz | 206/363 X |
| 4,142,632 | 3/1979 | Sandel | 206/363 |
| 4,151,913 | 5/1979 | Freitag | 206/63.3 X |
| 4,342,390 | 8/1982 | Mitchell et al. | 206/363 |

FOREIGN PATENT DOCUMENTS 855655 11/1952 Netherlands ........................ 211/13

Primary Examiner—J. Franklin Foss
Assistant Examiner—David L. Talbott
Attorney, Agent, or Firm—Alison C. Collard; Thomas M. Galgano

[57] ABSTRACT

A suture and surgical accessory rack includes a frame and bag-like disposable member supported in an upright manner on the frame. The bag-like member has a generally vertically-disposed front panel having secured thereto a multiplicity of first pockets, each configured and dimensioned for partial receipt therein of a suture-containing package, a needle count board including at least one numbered row to which used needles may be secured, and a surgical tie holder including a generally, horizontally-disposed wall member projecting outwardly from the front panel having a multiplicity of parallel, vertically-extending slits formed therein in which surgical ties may be individually inserted. The rack is intended for use by nurses during surgical procedures and it affords easy and facile access to various surgical accessories, monitors the number of needles and blades used and allows easy disposal in a safe manner.

23 Claims, 6 Drawing Figures

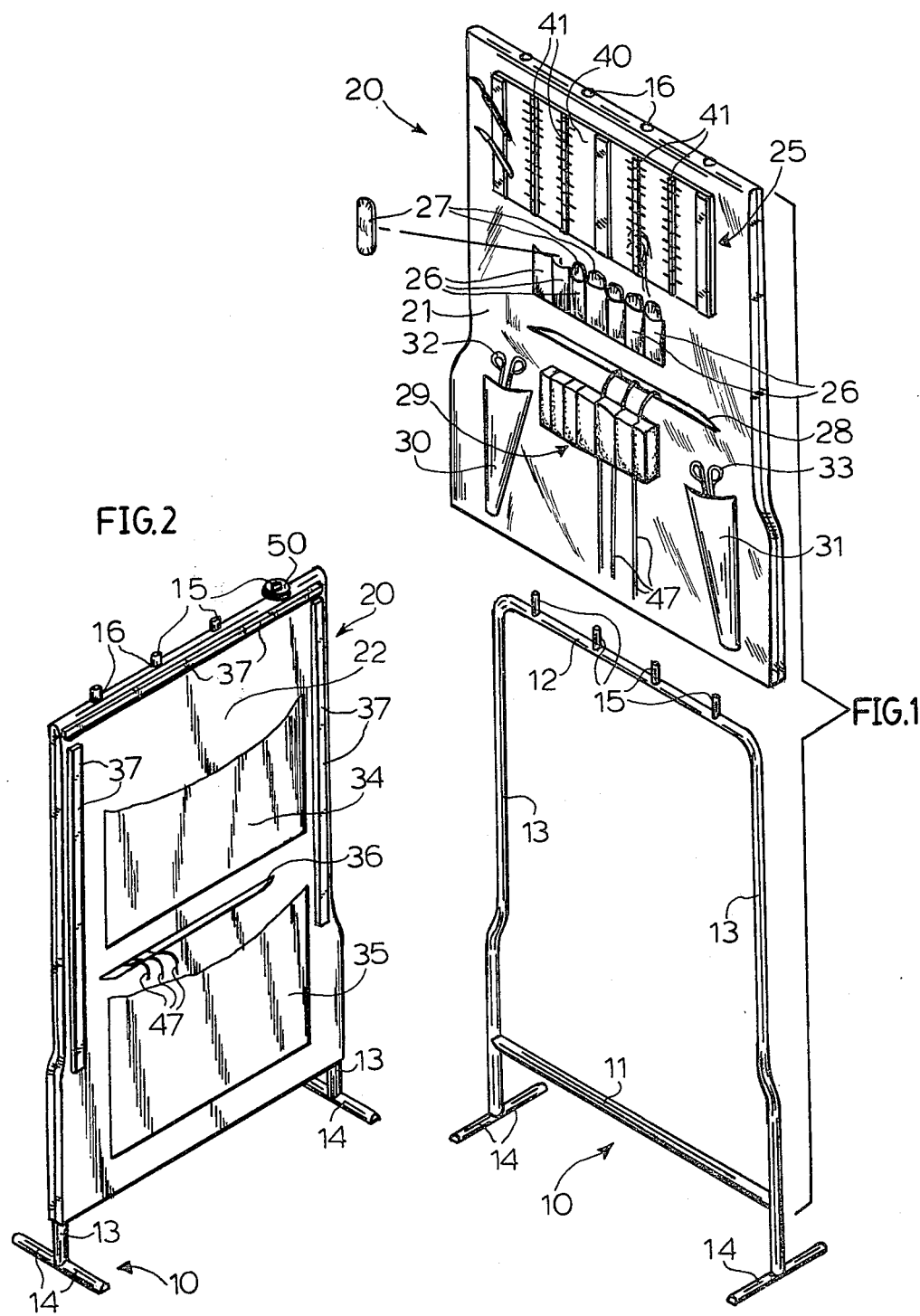

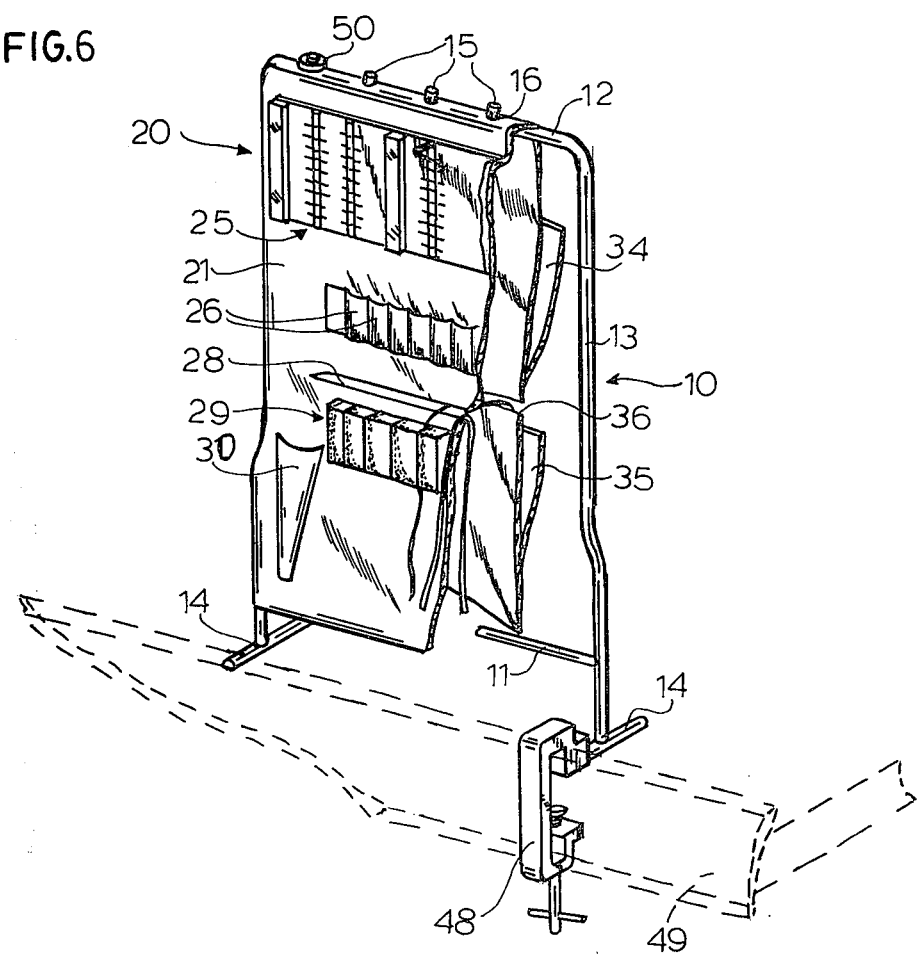

SUTURE AND SURGICAL ACCESSORY RACK

The present invention relates to a suture and surgical accessory rack.

During surgical procedures, it is the nurse's responsibility to quickly provide the surgeon with the surgical instruments and other surgical accessories, such as sutures, surgical ties, sponges, and the like, as requested by the surgeon during the operation. These surgical aids are typically laid out flat on an instrument table, commonly known as a "mayo" or on a back table. Keeping items on the back table most times is undesirable as the nurse must turn her back away from the surgeon. In addition, on either table, there is the problem that during the operation the surgical aids may get wet from saline or other surgical solutions or they may be dropped from the table or be misplaced, etc. Moreover, it is often difficult for the nurse to keep the various items in their proper place and in an orderly fashion, especially under demanding and intense surgical procedures. This presents a problem since before the doctor may suture the patient, the nurse must account for all surgical materials, particularly, the needles used for suturing, sponges, etc. and, if they are left haphazardly on the tables, this could delay the "count" and the completion of the operation, which could have serious consequences.

Up to the present time, so far as is known, no surgical aid has been proposed to assist the nurse in her many and varied duties during an operation, so as to enable her to quickly locate the requested sutures and other surgical accessory aids and to also keep track of the same following the completion of the operation and, at the same time, allow easy and safe disposal thereof and, in particular, safer than present methods of needle and blade disposal.

Accordingly, it is an object of the present invention to provide a novel suture and surgical accessory rack to aid nurses in surgical procedures.

It is a further object of the present invention to provide such a suture and surgical accessory rack which is disposable, sterile, easy to use and relatively inexpensive to fabricate, and in particular, safer than present methods of needle and blade disposal.

It is a more particular object of the present invention to provide such a novel surgical and suture rack which may store a variety of sutures and surgical ties and which allows one to keep track of used needles at all times during the operation.

Certain of the foregoing and related objects are readily attained in a suture and surgical accessory rack which includes a disposable member supportable in an upright manner having a generally, vertically-disposed front panel. The front panel has secured thereto a multiplicity of first pockets, each configured and dimensioned for partial receipt therein of a suture-containing package, a needle count board including at least one numbered row to which used needles may be secured, and a surgical tie holder including a generally, horizontally-disposed wall member projecting outwardly from said front panel having a multiplicity of parallel, vertically-extending slits formed therein in which surgical ties may be individually inserted.

Most advantageously, the disposable member is flexible and has a back panel joined to the front panel to define a bag-like member having a generally closed top end and an open bottom end. The back panel also preferably has a plurality of pockets for surgical dressings and items to be disposed of (e.g., empty suture packages, etc.). It is also desirable that the rack include a support on which the disposable member is mounted in an upright position. The support preferably comprises an upstanding, generally rectangular frame over which the bag-like member is received.

In a preferred embodiment, the frame has an upper, generally horizontally-disposed support member with a plurality of upstanding prongs configured for receipt thereon of reel ties and the top end of the bag-like member has a plurality of holes formed therein spaced and dimensioned to allow the prongs to be inserted therethrough when the bag-like member is mounted on the frame. The frame may have self-supporting feet and/or at least one foot fitted with a clamp for securing the same to a mayo or to be placed on a back table.

In a further advantageous embodiment, the front panel has a horizontally-disposed slit formed therethrough positioned above the wall member of the tie holder, the latter of which is preferably elastically deformable. It is also desirable that the numbered row of the needle count board be comprised of a raised rib of cushion-like material in which surgical needles may be inserted and retained thereby.

In a particularly preferred embodiment of the invention, at least one magnetic blade holder is secured to the front panel. In addition, the front panel has at least one pocket configured and dimensioned for receipt therein of a needle holder and at least one pocket configured and dimensioned for receipt therein of a pair of scissors.

Other objects and features of the present invention will become apparent from the following detailed description when taken in connection with the accompanying drawings which disclose several embodiments of the invention. It is to be understood that the drawings are designed for the purpose of illustration only and are not intended as a definition of the limits of the invention.

In the drawings, wherein similar reference characters denote similar elements throughout the several views:

FIG. 1 is a perspective view of a suture rack and frame assembly embodying the present invention showing the suture rack disposed above the frame prior to mounting thereon;

FIG. 2 is a view comparable to that of FIG. 1, but showing the rack in a fully mounted position;

FIG. 6 is a perspective view of the suture rack and frame assembly with the rack and frame partially broken away, further showing an alternate embodiment of the support feet therefor.

Figure 3:
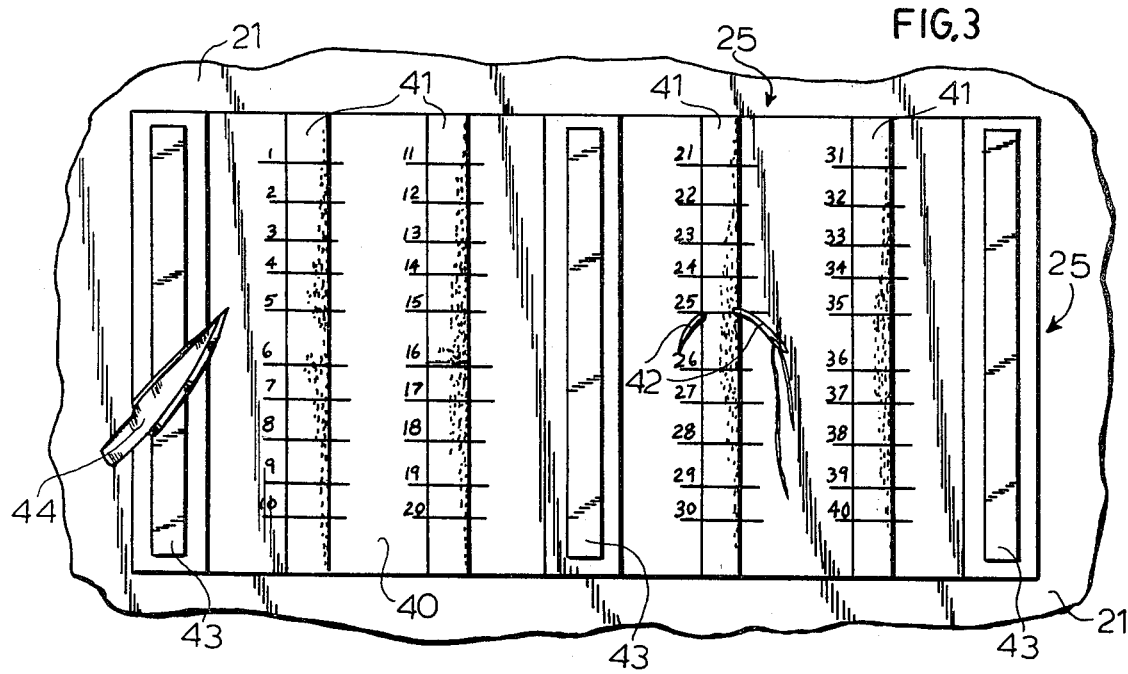
FIG. 3 is an enlarged, fragmentarily-illustrated front view of the needle count board.

Referring now in detail to the drawings and, in particular, FIGS. 1 and 2 thereof, therein illustrated is a novel suture and surgical accessory rack and stand assembly embodying the present invention which includes a tubular metal, generally rectangular frame 10 having a pair of horizontally-disposed lower and upper rod members 11 and 12 joined by a pair of upstanding leg members 13, each supported by a horizontally-extending foot 14. The upper frame rod 12 also has four spaced-apart, upstanding spikes or prongs 15 which are inserted into correspondingly, spaced-apart holes 16 formed in the top margin of a disposable, sterile, flexible bag-like member 20, preferably made of paper or plastic, which is received thereon. Both the bag 20 and the frame 10 are provided with complementary-configured flared lower portions which serve to afford a rather tight fit of the bag on the rack to afford a relatively secure mounting thereon.

The bag 20 has a front panel 21 and a rear panel 22. Front panel 21 has secured thereto a blade and needle count board 25, adjacent to the top margin thereof, a multiplicity of pockets 26 aligned in a horizontal row therebelow, each of which is configured for receipt therein of a sterilized package 27 containing a suture, i.e., a sterilized needle and thread. Immediately below the row of pockets 26 is a horizontally-disposed slot 28 below which is an outwardly-projecting tie holder 29. Below and to the sides of the tie holder 29 are a pair of pockets 30 and 31 in which a needle holder 32 and a scissors 33, respectively, are inserted.

The rear panel 22 has an upper and lower pocket 34 and 35, respectively, for surgical dressings and for items to be disposed of (e.g., empty suture packages, etc.). It also has a horizontally-disposed slot 36 in general alignment with slot 28 of the front panel 21 and three conventional releasable adhesive tape strips 37 which may be used to cover the slots 28, 36 and holes 16 after use of bag 20, as will be described in greater detail hereinafter. The adhesive strips 37 are each typically applied to a release strip (not shown) which would be secured to bag 20, but which would allow easy release of the strips 37 when desired.

As can be seen best in FIG. 3, the needle count board 25 consists of a generally planar panel 40 having four vertically spaced-apart rows defined by a raised rib or ridge 41 made of a preferably compressible foam plastic or fabric-like material in which a needle 42 may be readily inserted. Each row is subdivided by a multiplicity of vertically spaced-apart horizontal lines imprinted thereon and each such subdivision is consecutively numbered. During the operation, once a needle is used, it would be inserted into the ridge 41 of the first row adjacent to no. 1 and each successively-used needle would then be placed in the successive subdivision nos. 2, 3, 4, 5, etc. In this way, the nurse may keep constant track of the number of needles used. The needle count board also has a plurality of vertically-disposed, preferably plastic-encased magnetic bars or strips 43 interspaced thereon which will magnetically grip used blades 44.

Figure 4:
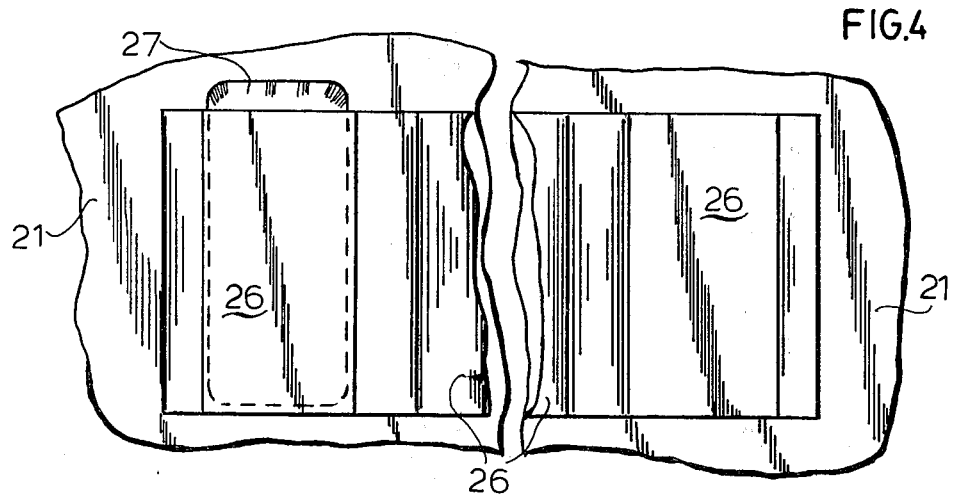
FIG. 4 is an enlarged, fragmentarily-illustrated front view of the suture-containing package pockets.

As shown in FIG. 4, the row of pockets 26 serve to each receive sterilized packages 27 of sutures. The pockets 26 are slightly undersized in terms of height to allow facile and easy grasping of the packages 27 by the nurse.

Figure 5:
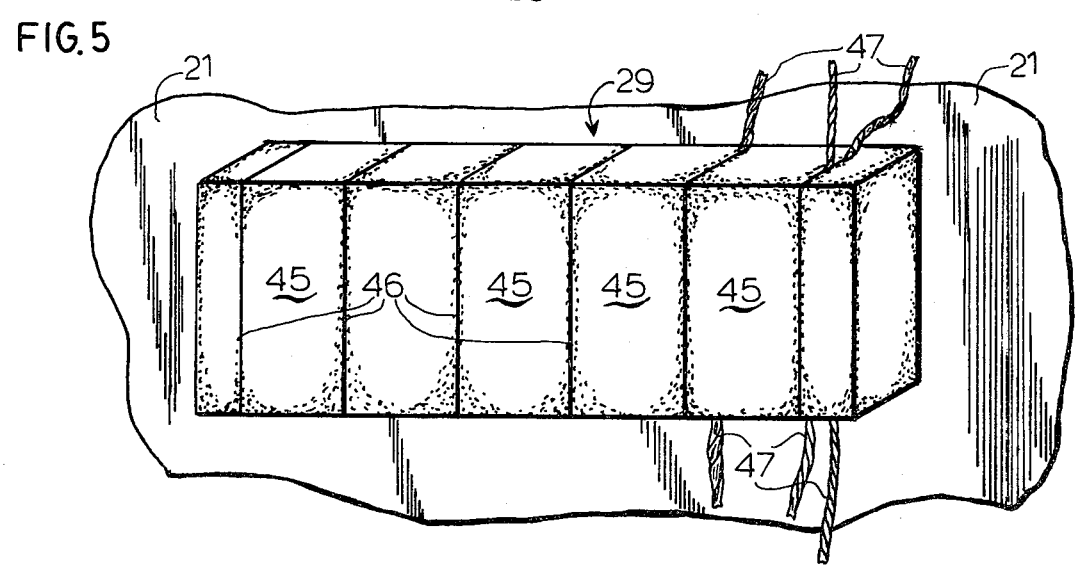
FIG. 5 is an enlarged, fragmentarily-illustrated perspective view of the surgical tie holder.

In FIG. 5, the surgical tie holder 29 is shown in greater detail and it includes a generally, outwardly-projecting wall member 45 made of an elastically-deformable, preferably foam plastic material in which a plurality of vertically-disposed slits 46 are formed. Between each of these slits, several ties 47 may be inserted and they may be arranged in each slit according to size. The ends of the ties 47 are inserted through slot 28 and slot 36 and are draped over the lip of slot 36 (see FIG. 2) to facilitate easy removal and grasping by the nurse.

As shown in FIG. 6, instead of having a selfsupporting stand, one or both of the feet 14 of the frame 10 may be provided with a C-shaped clamp 48 which, in turn, may be secured to the mayo edge 49.

As can be appreciated, during an operation, the inventive suture rack places the various surgical aids in easy reach of the nurse and may be placed on the instrument table without taking up too much space. As a result, it is not necessary to keep the surgical aids on a back table which would require the nurse to turn her back on the surgeon. In addition, the various surgical aids are conveniently located and are easily accessible. The nurse need not concern herself with maintaining the various items on the table in an orderly fashion, as this is already effected by the preset arrangement of the suture rack.

During the operation, when the surgeon calls for a particular type of suture, they are already aligned according to size and configuration in the pockets. This is true of the ties as well. In addition, reel-type ties 50 may be provided according to size on the spikes 15 of the rack 10.

Furthermore, once the surgical blades 44 are used, they may be simply attached to the magnetic strips 43 on the needle count board 25. The needle count board 25 can thus, of course, be used to keep track of all used blades 44, in addition to needles 42.

After the operation, the three releasable strips 37 may be placed over the slots 28, 36 and the row of holes 16 and the bag 20 may be turned inside-out and secured by a tie or other clasp and simply thrown away and replaced by a new sterile bag for the next operation.

It should, of course, be apparent that various modifications and changes may be made as will be apparent to those skilled in the art, although the presently-disclosed embodiments appear to offer the most advantageous arrangement and combination of features. For example, the number and placement of the various pockets may be altered. In addition, various materials may be employed for the various components. Further, while bag-like envelope is advantageously used to allow for secure mounting and easy disposal, a single sheet of material could possibly be employed. Moreover, other types of supports for the suture rack may be found suitable.

Thus, while only several embodiments of the present invention have been shown and described, it will be obvious that many changes and modifications may be made thereunto, without departing from the spirit and scope of the invention.

What is claimed is:

1. A suture and surgical accessory rack, comprising; a disposable sterile member supportable in an upright manner, having a generally, vertically-disposed front panel, said front panel having secured thereto a multiplicity of first pockets, each configured and dimensioned for partial receipt therein of a suture-containing package, a needle count board including at least one numbered row to which used needles may be secured, and a surgical tie holder including a generally, horizontally-disposed wall member projecting outwardly from said front panel having a multiplicity of parallel, vertically-extending slits formed therein in which surgical ties may be individually inserted, said front panel having a horizontally-disposed slit formed therethrough positioned above said wall member of said tie holder.

2. The rack according to claim 1, wherein said disposable member is flexible and has a back panel joined to the front panel to define a bag-like member having a generally closed top end and an open bottom end.

3. The rack according to claim 2, wherein said back panel has a plurality of pockets for surgical dressings.

4. The rack according to claim 2, additionally including a support on which said disposable member is mounted in an upright position.

5. The rack according to claim 4, wherein said support comprises an upstanding, generally rectangular frame over which said bag-like member is received.

6. The rack according to claim 5, wherein said frame has an upper, generally horizontally-disposed support member with a plurality of upstanding prongs configured for receipt thereon of reel ties and wherein said top end of said bag-like member has a plurality of holes formed therein spaced and dimensioned to allow said prongs to be inserted therethrough when said bag-like member is mounted on said frame.

7. The rack according to claim 6, wherein said frame has self-supporting feet.

8. The rack according to claim 6, wherein said frame has at least one foot fitted with a clamp for securing the same to a table.

9. The rack according to claim 1, wherein said wall member is elastically deformable.

10. The rack according to claim 1, wherein said numbered rows of said needle count board is comprised of a raised rib of cushion-like material in which surgical needles may be inserted and retained thereby.

11. The rack according to claim 1, wherein at least one magnetic blade holder is secured to said front panel.

12. The rack according to claim 1, wherein said front panel has at least one pocket configured and dimensioned for receipt therein of a needle holder.

13. The rack according to claim 1, wherein said front panel has at least one pocket configured and dimensioned for receipt therein of a pair of scissors.

14. A suture and surgical accessory rack, comprising; a disposable, sterile, flexible member having a front panel and a back panel joined together so as to define a bag-like member having a closed top end and an open bottom end, said member being supportable in an upright manner such that said front panel is generally vertically disposed, said front panel having secured thereto a multiplicity of first pockets, each configured and dimensioned for partial receipt therein of a suture-containing package, a needle count board including at least one numbered row to which used needles may be secured, and a surgical tie holder including a generally, horizontally-disposed wall member projecting outwardly from said front panel having a multiplicity of parallel, vertically-extending slits formed therein in which surgical ties may be individually inserted; and, an upstanding, generally rectangular frame over which said bag-like member is removably received in an upside-down manner with said bottom open end facing downwardly, said bag being removable from said frame and being capable of being turned inside-out so as to define a refuse receptacle.

15. The rack according to claim 14, wherein said frame has an upper, generally horizontally-disposed support member with a plurality of upstanding prongs configured for receipt thereon of reel ties and wherein said top end of said bag-like member has a plurality of holes formed therein spaced and dimensioned to allow said prongs to be inserted therethrough when said bag-like member is mounted on said frame.

16. The rack according to claim 15, wherein said frame has self-supporting feet.

17. The rack according to claim 15, wherein said frame has at least one foot fitted with a clamp for securing the same to a table.

18. The rack according to claim 14, wherein said front panel has a horizontally-disposed slit formed therethrough positioned above said wall member of said tie holder.

19. The rack according to claim 14, wherein said wall member is elastically deformable.

20. The rack according to claim 14, wherein said numbered rows of said needle count board is comprised of a raised rib of cushion-like material in which surgical needles may be inserted and retained thereby.

21. The rack according to claim 14, wherein at least one magnetic blade holder is secured to said front panel.

22. The rack according to claim 14, wherein said front panel has at least one pocket configured and dimensioned for receipt therein of a needle holder.

23. The rack according to claim 14, wherein said front panel has at least one pocket configured and dimensioned for receipt therein of a pair of scissors.

* * * * *